United States Patent
Smith et al.

(10) Patent No.: US 9,481,844 B2
(45) Date of Patent: Nov. 1, 2016

(54) PROCESS AND ADSORBENT FOR REMOVAL OF DIOLEFINS AND OTHER CONTAMINANTS FROM LIQUEFIED PETROLEUM GAS

(71) Applicant: UOP LLC, Des Plaines, IL (US)

(72) Inventors: Edward F. Smith, Roselle, IL (US); Erick D. Gamas-Castellanos, Houston, TX (US)

(73) Assignee: UOP LLC, Des Plaines, IL (US)

( * ) Notice: Subject to any disclaimer, the term of this patent is extended or adjusted under 35 U.S.C. 154(b) by 380 days.

(21) Appl. No.: 14/100,971

(22) Filed: Dec. 9, 2013

(65) Prior Publication Data

US 2015/0158797 A1      Jun. 11, 2015

(51) Int. Cl.
 *C07C 7/12* (2006.01)
 *C07C 7/13* (2006.01)
 *C07C 7/148* (2006.01)
 *C07C 7/152* (2006.01)
 *C10L 3/12* (2006.01)

(52) U.S. Cl.
 CPC . *C10L 3/12* (2013.01); *C07C 7/13* (2013.01); *C07C 7/12* (2013.01)

(58) Field of Classification Search
 USPC ........ 585/810, 809, 823, 824, 826, 829, 860
 See application file for complete search history.

(56) References Cited

U.S. PATENT DOCUMENTS

| | | | |
|---|---|---|---|
| 2,943,105 A * | 6/1960 | Caruthers | C07C 29/76 518/722 |
| 3,596,436 A * | 8/1971 | Dassesse | C07C 7/12 95/108 |
| 6,440,885 B1 | 8/2002 | Pierotti et al. | |
| 6,977,067 B2 | 12/2005 | Hwang et al. | |
| 7,074,375 B2 | 7/2006 | Lampert et al. | |
| 8,008,223 B2 | 8/2011 | Garcia-Martinez | |
| 2002/0043154 A1 | 4/2002 | Shore | |
| 2009/0023882 A1 * | 1/2009 | Hanefeld | C08F 110/10 526/348.7 |
| 2009/0216059 A1 | 8/2009 | Reyes et al. | |

FOREIGN PATENT DOCUMENTS

| | | |
|---|---|---|
| EP | 0055535 A1 | 7/1982 |
| EP | 1128897 A1 | 9/2001 |
| WO | 0020105 A1 | 4/2000 |

* cited by examiner

*Primary Examiner* — Thuan D Dang

(57) ABSTRACT

A process and an apparatus for reducing the diolefin and oxygenate content of liquefied petroleum gas are disclosed. A first conduit is in fluid communication with a liquefied hydrocarbon source and a vessel. The vessel includes a solid adsorbent disposed on a support. The adsorbent is suitable for adsorbing diolefins and oxygenates. A second conduit is in fluid communication with the vessel for receiving the liquefied hydrocarbons of reduced diolefin and oxygenate content from the vessel. A steam inlet conduit is in fluid communication with a steam source and the vessel for treating the solid adsorbent containing adsorbed diolefins and oxygenates with steam to desorb the diolefins and oxygenates from the solid adsorbent. An amine absorber unit for reducing the hydrogen disulfide content of the liquefied hydrocarbon can be in fluid communication with the vessel.

6 Claims, 3 Drawing Sheets

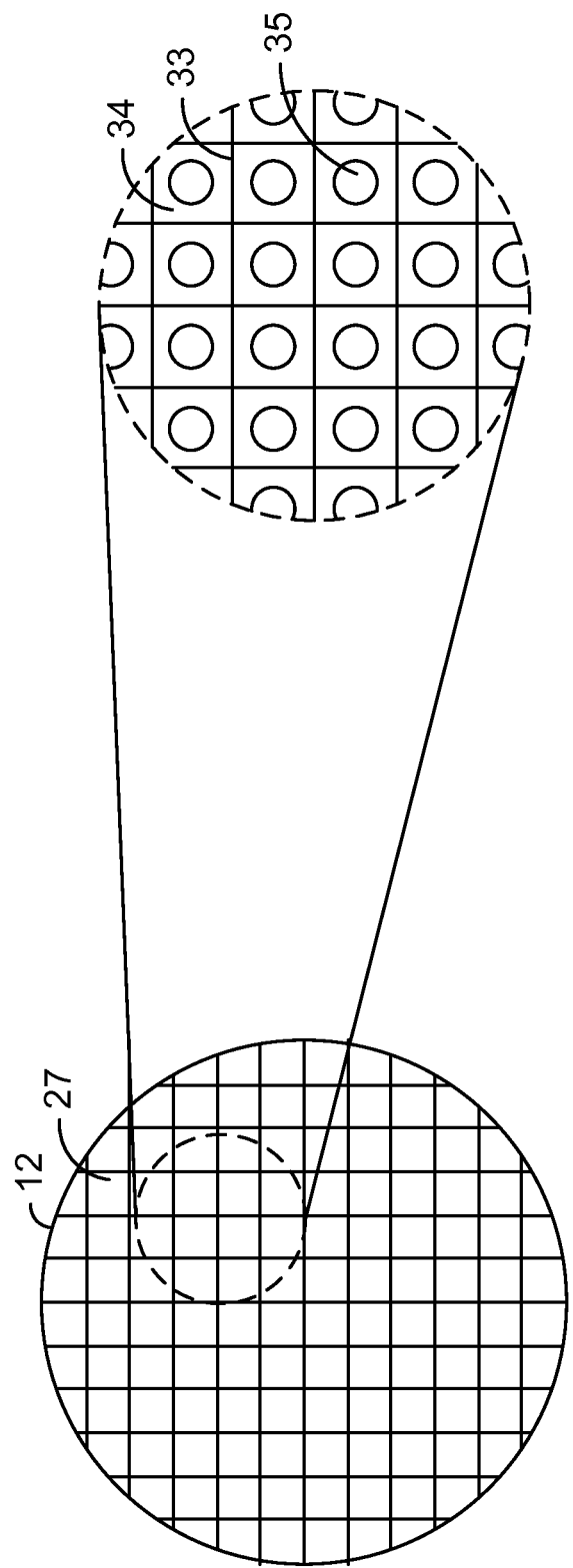

PROCESS AND ADSORBENT FOR REMOVAL OF DIOLEFINS AND OTHER CONTAMINANTS FROM LIQUEFIED PETROLEUM GAS

BACKGROUND

This invention generally relates to a pretreatment process for liquefied petroleum gas. One of the products of fluid catalytic cracking (FCC) is liquefied petroleum gas (LPG). LPG, which generally comprises 3 and 4 carbon alkanes and alkenes, often contains impurities in the form of sulfur containing compounds such as hydrogen sulfide and mercaptans. In the oil refining industry, it is conventional practice to treat sour hydrocarbon streams to remove these sulfur species. Extraction processes are typically used when treating light hydrocarbons for hydrogen sulfide and mercaptan removal. Mercaptans have traditionally been removed from hydrocarbon streams because of their malodorous scent and contribution to product total sulfur.

In a typical configuration, a liquid LPG stream is fed to an amine absorber column to be contacted with an amine, such as diethanolamine (DEA) or methyldiethanol amine (MDEA), to absorb acid gases such as hydrogen sulfide and carbon dioxide. The LPG lean of hydrogen sulfide and other acid gases is then sent on for further treating to remove mercaptan sulfur compounds before it is sent to product storage or a downstream processing unit.

LPG derived from high severity, high propylene FCC units contains higher concentrations of diolefins and other impurities (such as oxygenates), which have been found to contribute to foaming in the amine absorber. Removal of these materials is envisioned as a pretreatment solution to eliminate these impurities and resolve foaming issues that would otherwise occur during the amine absorption process. However, modification of the upstream process can have a strong impact on the overall process and on the operating costs.

Therefore, a process is needed to remove impurities upstream of the amine absorber without disturbing the overall LPG treating operation.

SUMMARY

One embodiment of the present disclosure relates to the adsorption of the diolefin and oxygenate impurities in a pretreatment vessel containing a packing material such as a monolith washcoated with an appropriate adsorbent material. Monoliths, or monolithic structures, are a solid structure that includes a number of channels, often parallel with each other. The cross-sectional shape of the channel may be circular, hexagonal, square, triangular or sinusoidal. Monoliths are useful structures for a number of applications as they can be coated with materials such as catalysts or adsorbents. Some applications of monoliths include automobile catalytic converters, catalytic combustion, electrochemical reactors, biochemical reactors and the like. In order to coat, or washcoat, the honeycomb-like structure of the monolith, a slurry will be prepared containing the adsorbent material as well as a binder to promote adherence of the adsorbent to the internal walls of the channels of the monolith.

It is therefore an advantage of the invention to provide a process to remove contaminants upstream of an amine absorber without disturbing an overall liquefied petroleum gas treating operation.

These and other features, aspects, and advantages of the present invention will become better understood upon consideration of the following detailed description, drawings and appended claims.

BRIEF DESCRIPTION OF THE DRAWINGS

FIG. 3 is a cross-section taken along the line 3-3 of FIG. 1.

FIG. 4 is an enlarged view of FIG. 3.

Like reference numerals will be used to refer to like parts from Figure to Figure in the following description of the drawings.

DETAILED DESCRIPTION

A general understanding of the process and apparatus of this invention can be obtained by reference to the Figures. The Figures have been simplified by the deletion of a large number of apparatuses customarily employed in a process of this nature, such as vessel internals, temperature and pressure controls systems, flow control valves, circulation pumps, etc. which are not specifically required to illustrate the performance of the invention. Furthermore, the illustration of the process of this invention in the embodiment of a specific drawing is not intended to limit the invention to specific embodiments set out herein. Lastly, although a process for pretreatment of LPG is illustrated by way of an example, other LPG pretreatment schemes are contemplated.

Figure 1:
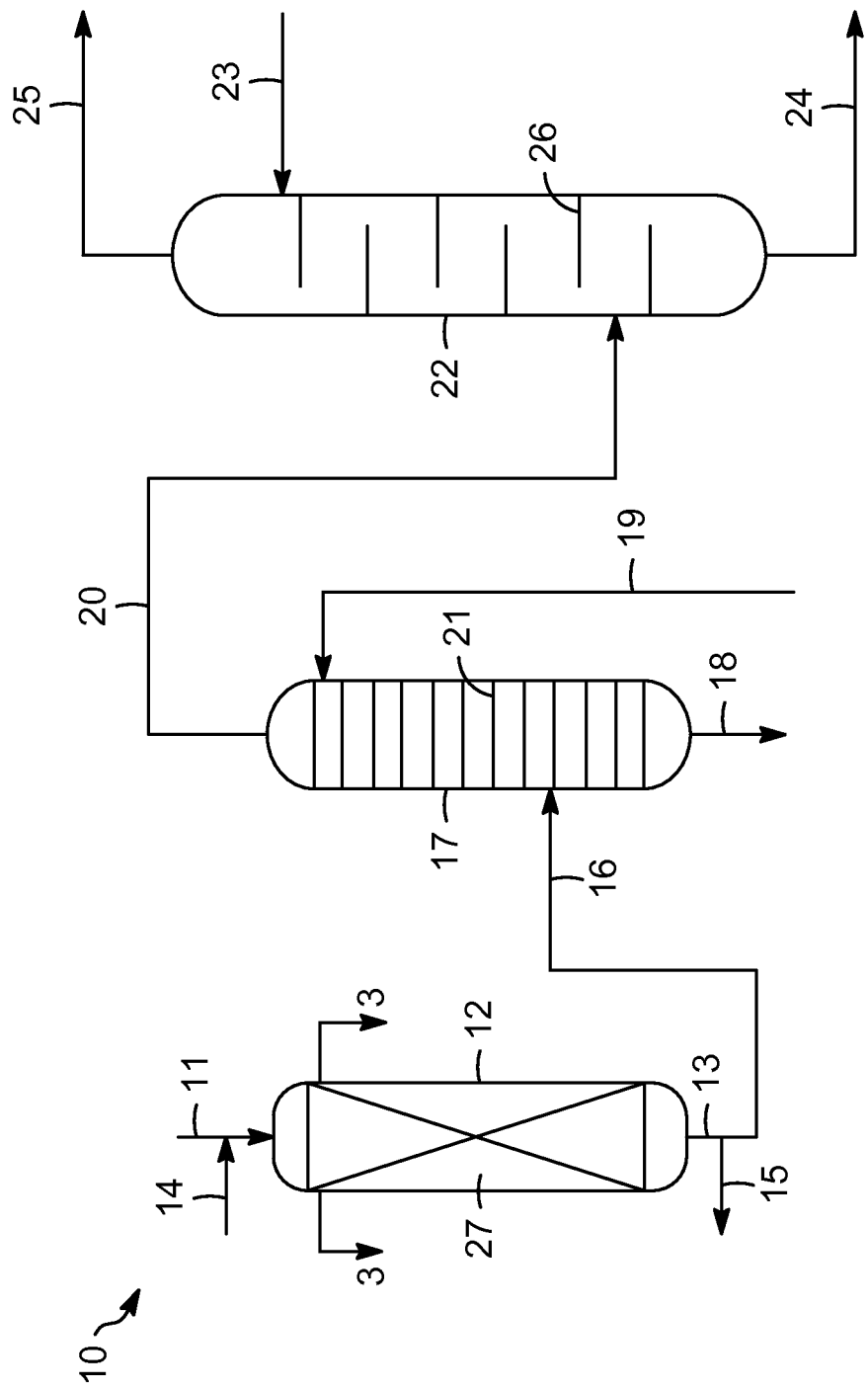
FIG. 1 is a schematic of an LPG treatment unit comprising an LPG pretreatment vessel containing the monolith, an amine absorber, and a mercaptan extractor.

FIG. 1 illustrates a unit operation 10 for the treatment of a liquefied petroleum gas (LPG) stream. Referring to FIG. 1, a hydrocarbon liquid stream such as LPG containing diolefins and oxygenates in addition to mercaptan sulfur and hydrogen sulfide is fed through a line 11 to a pretreatment vessel 12. The pretreatment vessel 12 contains a packing material 27 which comprises an adsorbent 34 deposited on a solid support 33 as depicted in FIGS. 3-4 in greater detail. The hydrocarbon stream can pass over the packing material 27 and exit the pretreatment vessel 12 through a line 13.

Over time, the packing material 27 in the pretreatment vessel 12 will have adsorbed a significant amount of the diolefin and oxygenate impurities and will need to be regenerated. This regeneration process can be accomplished by contacting the packing material with a regenerative gas such as steam. A steam source is in fluid communication with the pretreatment vessel 12 by way of a steam inlet conduit 14. Steam that has contacted the packing material 27 can then exit the vessel by way of a steam outlet conduit 15.

After exiting the pretreatment vessel 12, the hydrocarbon stream with a reduced diolefin and oxygenate content can be sent to an amine absorber vessel 17 to reduce the amount of hydrogen sulfide in the hydrocarbon stream. The hydrocarbon stream enters the amine absorber 17 through a line 16. Amines such as diethanolamine (DEA), methyldiethanolamine (MDEA), or others are fed to the amine absorber vessel 17 through a line 19. The amine absorber vessel 17 contains a series of liquid-liquid contacting trays 21. The line 16 delivering the hydrocarbon stream has an inlet distributor that is above the bottom feed tray of vessel 17. Amine enters at the top tray of vessel 17 via line 19 to allow counter-current contact of the amine descending down and the hydrocarbon ascending up the vessel 17. The amine in vessel 17 reacts with hydrogen sulfide to yield amine sulfide salts. Typically, hydrogen sulfide content of a hydrocarbon stream is reduced down to 50 wppm or less. An amine effluent stream rich in acid gas exits the bottom of the amine absorber vessel 17 through a line 18 while the hydrocarbon effluent stream exits the top of the amine absorber vessel 17 through a line 20 with a substantially reduced concentration of hydrogen sulfide. Additionally, carbon dioxide or other acid gases that are possibly present in the feed stream in the line 16 also react with the amines and are absorbed into the amine effluent stream leaving the amine absorber vessel 17 through the line 18.

The hydrocarbon effluent from the amine absorber vessel 17 enters an extraction vessel 22 through the line 20. The purpose of this vessel is to remove mercaptan sulfur compounds from the hydrocarbon stream. An alkaline solution rich in mercaptans is withdrawn from the extraction vessel 22 through a line 24. Fresh or regenerated alkaline in a line 23 is continuously fed to the extraction vessel 22. Mercaptans in the extraction vessel 22 react with the an alkaline solution (e.g., sodium hydroxide) to yield sodium mercaptides and water. The lower density hydrocarbons rise to the top of the extraction vessel 22 while the aqueous alkaline containing dissolved mercaptides flows to the bottom of the extraction vessel 22. Treated hydrocarbon substantially devoid of mercaptans and mercaptides exits the extraction vessel 22 via a product line 25. Alkaline rich in mercaptides is withdrawn through a line 24.

Figure 2:
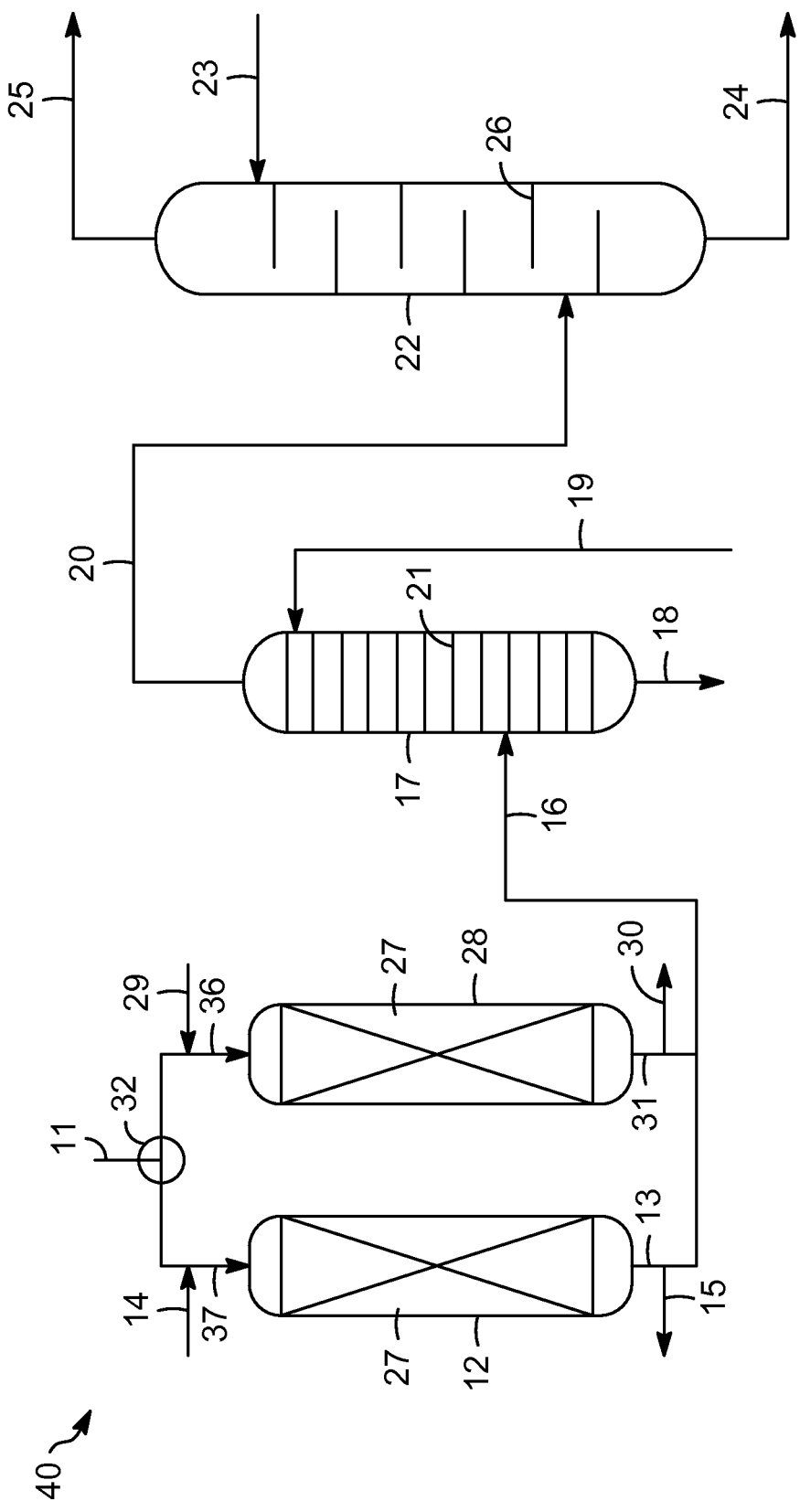
FIG. 2 is an alternate embodiment of the LPG treatment unit comprising a second LPG pretreatment vessel containing the monolith.

FIG. 2 shows an alternate embodiment of the LPG treatment unit 40 comprising a second pretreatment vessel 28 which also contains the packing material 27. The advantage of a second pretreatment vessel 28 is the ability to direct the hydrocarbon stream from line 11 into either the first pretreatment vessel 12 through the line 37 or the second pretreatment vessel 28 through the line 36. A control valve 32 can be used to determine to which downstream line the hydrocarbon stream in line 11 flows. Furthermore, a steam source is in fluid communication with both the first pretreatment vessel 12 by way of steam inlet conduit 14 and the second pretreatment vessel 28 by way of steam inlet conduit 29. Steam outlet conduit 15 and steam outlet conduit 30 allow for steam to leave pretreatment vessel 12 and pretreatment vessel 28, respectively.

FIG. 3 is a cross-section taken along the line 3-3 of FIG. 1. FIG. 3 shows the internals of a pretreatment vessel 12 according to the invention in greater detail. The pretreatment vessel 12 contains a packing material 27 that extends across the entire cross-sectional area of the pretreatment vessel 12 and contacts the inner wall of the pretreatment vessel 12. The packing material, as seen in greater detail in FIG. 4, is comprised primarily of an adsorbent 34 disposed on a solid support 33. In one embodiment of the present invention, the support material is a monolithic support comprised of cordierite. In another embodiment, the monolithic support is comprised of straight parallel microcells. Regarding the adsorbent, the material must be capable of adsorbing diolefins and oxygenates from the hydrocarbon stream. Examples of adsorbents that are suitable for the present invention include zeolites such as ZSM-5, ZSM-11, ZSM-12, ZSM-23, ZSM-35, ZSM-38, ZSM-48, metal organic frameworks, and alumina.

If a monolithic form of support is desired, the adsorbent is applied to the monolithic form as a thin film or coating deposited on the monolith. The inert monolithic carrier can be comprised of any inert material which provides the structural support for the adsorbent. Usually this material can be any refractory material such as ceramic or metallic materials. It is desirable that the carrier material be unreactive with the adsorbent and adsorbent components and not be degraded by the hydrocarbon to which it is exposed. Examples of suitable ceramic support materials include sillimanite, petalite, cordierite, mullite, zircon, zircon mullite, spodumene, alumina-titanate, etc. Metallic materials which are within the scope of this invention include metals and alloys that have an oxide layer such as steel having an alumina layer protecting the steel substrate against oxidation attack. Suitable monoliths may be obtained from Corning Incorporated of Corning, N.Y. and from Lexco, Inc. of Hudson, Ohio.

The support material 33 can best be utilized in any rigid unitary configuration which provides a plurality of pores or channels extending in the direction of gas flow. It is preferred that the configuration be a honeycomb configuration. The honeycomb structure can be used advantageously in either unitary form, or as an arrangement of multiple modules. The honeycomb structure is usually oriented such that hydrocarbon flow is generally in the same direction as the cells or channels of the honeycomb structure. The adsorbent is deposited onto the support material 33 by any convenient way well known in the art. A preferred method involves preparing a slurry of the adsorbent and a binder, and coating the monolithic honeycomb carrier with the slurry. The adsorbent should be about 10 to about 30 wt % of the slurry and preferably about 20 to about 25 wt % of the slurry. The binder may comprise an alumina, silica or a zirconia.

The slurry can be prepared by means known in the art. An inorganic slurry can be prepared by combining the appropriate amount of the adsorbent and binder with water and a peptizing agent that may be an acid such as nitric acid. About twenty five to thirty five parts of water to one part of acid will be sufficient. Alternatively, sols of alumina, silica or zirconia may be mixed with the adsorbent and a peptizing agent acid to provide the inorganic slurry. Additionally, inorganic salts such as aluminum chloride, and/or hydrolysis products or hydroxides of aluminum, silica or zirconium may be mixed with the adsorbent to provide the slurry. An organic slurry can include an organic polymer such as Methocel, organic salts of aluminum such as co-alkyl aluminum, silica or zirconium or organic silicates that are hydrolyzable to silica may be mixed with the adsorbent. Mixtures of the described binders are also contemplated; organic silicates that are hydrolyzable to silica; and mixtures thereof.

This mixture is then blended by using means such as sonification, milling, or another suitable method to provide the slurry. This slurry may be used to wash coat a monolithic honeycomb by dipping the honeycomb into the slurry and removing the excess slurry by draining or blowing out the channels. The desired slurry of adsorbent material may be deposited onto the support in any suitable manner well known in the art. In some embodiments, the adsorbent material 34 is disposed on the solid support 33 by brushing or spraying the liquid slurry of adsorbent onto the walls of the support.

The coated support is heated to about 100 to about 120° C. to dry the coated support. The dried support should then be calcined at over about 600° C. to bond the adsorbent to the support or to decompose the organic material from the support. If the desired loading of support is not achieved, the above process may be repeated as many times as required to achieve the desired loading.

The process of disposing of the adsorbent material 34 onto the solid support 33 leaves channels 35 through which the hydrocarbon stream may flow. The channels 35 allow for the hydrocarbon stream to contact the adsorbent material 34 within the pretreatment vessel 12. This arrangement assures adequate contact between the hydrocarbon and the adsorbent in order to efficiently adsorb diolefins and oxygenate contaminants from the hydrocarbon stream.

In general, the pretreatment vessel 12 may have a diameter of about 30 cm (1 foot) to about 762 cm (25 feet). Preferably, the diameter is about 61 cm (2 feet) to about 457 cm (15 feet). More preferably, the diameter is about 91 cm (3 feet) to about 366 cm (12 feet). Ideally, the diameter is about 107 cm (3.5 feet) to about 305 cm (10 feet). In general, the pretreatment vessel 12 may have a height of about 152 cm (5 feet) to about 76.2 m (250 feet). Preferably, the height is about 305 cm (10 feet) to about 45.7 m (150 feet). More preferably the height is about 457 cm (15 feet) to about 30.5 m (100 feet). Ideally, the height is about 610 cm (20 feet) to about 15.2 m (50 feet).

In some embodiments of the present invention, the microcells of the solid support have about 650 to about 3900 cells per $cm^2$ (about 100 to about 600 cells per square inch). Preferably, the microcells of the solid support have about 1300 to about 2600 cells per $cm^2$ (about 200 to about 400 cells per square inch). Ideally the microcells of the solid support have about 1950 to about 3250 cells per $cm^2$ (about 300 to about 500 cells per square inch).

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

Specific Embodiments

While the following is described in conjunction with specific embodiments, it will be understood that this description is intended to illustrate and not limit the scope of the preceding description and the appended claims.

A first embodiment of the invention is a process for reducing the diolefin and oxygenate content of a liquefied $C_2$-$C_5$ hydrocarbon, the process comprising feeding the liquefied hydrocarbon to a vessel containing a solid adsorbent disposed on a support thereby adsorbing the diolefins and oxygenates on the adsorbent. An embodiment of the invention is one, any or all of prior embodiments in this paragraph up through the first embodiment in this paragraph, further comprising treating the solid adsorbent containing adsorbed diolefins and oxygenates with steam to separate the adsorbed diolefins and oxygenates from the solid adsorbent. An embodiment of the invention is one, any or all of prior embodiments in this paragraph up through the first embodiment in this paragraph, wherein the solid adsorbent is a zeolite. An embodiment of the invention is one, any or all of prior embodiments in this paragraph up through the first embodiment in this paragraph, wherein the solid adsorbent is a metal organic framework. An embodiment of the invention is one, any or all of prior embodiments in this paragraph up through the first embodiment in this paragraph, wherein the solid adsorbent is alumina. An embodiment of the invention is one, any or all of prior embodiments in this paragraph up through the first embodiment in this paragraph, wherein the support is a monolithic support. An embodiment of the invention is one, any or all of prior embodiments in this paragraph up through the first embodiment in this paragraph, wherein the monolithic support is cordierite. An embodiment of the invention is one, any or all of prior embodiments in this paragraph up through the first embodiment in this paragraph, wherein the monolithic support comprises straight parallel microcells. An embodiment of the invention is one, any or all of prior embodiments in this paragraph up through the first embodiment in this paragraph, wherein the solid adsorbent is disposed on the microcells of the monolithic support by forming a slurry comprising the adsorbent and wash coating the microcells with the slurry. An embodiment of the invention is one, any or all of prior embodiments in this paragraph up through the first embodiment in this paragraph, further comprising passing the liquefied hydrocarbon of reduced diolefin and deoxygenate content to an amine absorber unit, wherein the amine absorber unit reduces the hydrogen disulfide content of the liquefied hydrocarbon.

A second embodiment of the invention is an apparatus for reducing the diolefin and oxygenate content of a liquefied $C_2$-$C_5$ hydrocarbon, the apparatus comprising a first conduit in fluid communication with a liquefied hydrocarbon source and a vessel, the vessel comprising solid adsorbent disposed on a support, the adsorbent suitable for adsorbing diolefins and oxygenates; and a second conduit in fluid communication with the vessel for receiving the liquefied hydrocarbons of reduced diolefin and oxygenate content from the vessel. An embodiment of the invention is one, any or all of prior embodiments in this paragraph up through the second embodiment in this paragraph, further comprising a steam inlet conduit in fluid communication with a steam source and the vessel for treating the solid adsorbent containing adsorbed diolefins and oxygenates with steam to desorb the diolefins and oxygenates from the solid adsorbent; and a steam outlet conduit in fluid communication with the vessel for removing steam from the vessel. An embodiment of the invention is one, any or all of prior embodiments in this paragraph up through the second embodiment in this paragraph, wherein the solid adsorbent is a zeolite. An embodiment of the invention is one, any or all of prior embodiments in this paragraph up through the second embodiment in this paragraph, wherein the solid adsorbent is a metal organic framework. An embodiment of the invention is one, any or all of prior embodiments in this paragraph up through the second embodiment in this paragraph, wherein the solid adsorbent is selected from alumina and cordierite. An embodiment of the invention is one, any or all of prior embodiments in this paragraph up through the second embodiment in this paragraph, wherein the support is a monolithic support. An embodiment of the invention is one, any or all of prior embodiments in this paragraph up through the second embodiment in this paragraph, wherein the monolithic support comprises straight parallel microcells. An embodiment of the invention is one, any or all of prior embodiments in this paragraph up through the second embodiment in this paragraph, further comprising an amine absorber unit for reducing the hydrogen disulfide content of the liquefied hydrocarbon, the amine absorber unit being in fluid communication with the vessel.

A third embodiment of the invention is an apparatus for reducing the diolefin and oxygenate content of a liquefied $C_2$-$C_5$ hydrocarbon, the apparatus comprising a first conduit in fluid communication with a liquefied hydrocarbon source and a vessel, the vessel comprising solid adsorbent disposed on a support, the adsorbent suitable for adsorbing diolefins and oxygenates; a second conduit in fluid communication with the vessel for receiving the liquefied hydrocarbons of reduced diolefin and oxygenate content from the vessel; and a second vessel in fluid communication with the liquefied hydrocarbon source, the steam inlet conduit and the steam outlet conduit, the second vessel comprising the solid adsorbent disposed on a support thereby to adsorb the diolefins and oxygenates. An embodiment of the invention is one, any or all of prior embodiments in this paragraph up through the third embodiment in this paragraph, wherein the liquefied hydrocarbon source can be passed to either the first vessel or the second vessel to allow for the vessel that is not in contact with the liquefied hydrocarbon to be regenerated by contacting the solid adsorbent in the vessel with steam.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for reducing the diolefin and oxygenate content of a liquefied $C_2$-$C_5$ hydrocarbon, the process comprising feeding the liquefied hydrocarbon to a vessel containing a solid adsorbent disposed on a support thereby adsorbing the diolefins and oxygenates on the adsorbent, wherein the support is a monolithic support and solid adsorbent is disposed on microcells of the monolithic support and wherein the solid adsorbent is ZSM-5, ZSM-11, ZSM-12, ZSM-23, ZSM-35, ZSM-38, or ZSM-48; and passing the liquefied hydrocarbon of reduced diolefin and oxygenate content to an amine absorber unit, wherein the amine absorber unit reduces the hydrogen disulfide content of the liquefied hydrocarbon with less foaming in the amine absorber unit as compared to a liquefied hydrocarbon without reduced diolefin and oxygenate content.

2. The process of claim 1, further comprising treating the solid adsorbent containing adsorbed diolefins and oxygenates with steam to separate the adsorbed diolefins and oxygenates from the solid adsorbent.

3. The process of claim 1, wherein the monolithic support is cordierite.

4. The process of claim 1, wherein the monolithic support comprises straight parallel microcells.

5. The process of claim 1 wherein the solid adsorbent is disposed on the microcells of the monolithic support by forming a slurry comprising the adsorbent and wash coating the microcells with the slurry.

6. The process of claim 1 wherein the solid adsorbent is disposed on the microcells of the monolithic support by forming a slurry comprising the adsorbent and a binder, the adsorbent being about 10 to about 30 wt % of the slurry.

* * * * *